US00PP32477P2

(12) United States Plant Patent
Hoogendoorn

(10) Patent No.: US PP32,477 P2
(45) Date of Patent: Nov. 17, 2020

(54) ***ALICEARA* ORCHID PLANT NAMED 'CAMBAMIM'**

(50) Latin Name: ***Nothogemus* x *Aliceara***
Varietal Denomination: CAMBAMIM

(71) Applicant: ANTHURA B.V., Bleiswijk (NL)

(72) Inventor: Gert-Jan Hoogendoorn, Woubrugge (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/602,488

(22) Filed: Oct. 17, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of x *Aliceara* plant named 'CAMBAMIM', particularly characterized by having large, cream-white flowers with dark red flecks and large, undulated white lips with 1-3 dark red flecks, 1-3 peduncles that are long and sturdy, leaves that are lanceolate and elongated to very elongated, and is propagated by meristem tissue culture is disclosed.

3 Drawing Sheets

Genus and species: *Nothogenus:* x *Aliceara.*
Variety denomination 'CAMBAMIM'.

BACKGROUND OF THE NEW PLANT

The present invention comprises a new and distinct cultivar of x *Aliceara* plant, botanically known as x *Aliceara* of the Orchidaceae family, and hereinafter referred to by the cultivar name 'CAMBAMIM'.

*Miltonia, Oncidium, Brassia*, and some other genera are a complex group of orchid species that are easily hybridized. The boundaries between the genera have been under discussion for the last several decades. According to the most recent classification by Pridgeon, Cribb, Chase, and Rasmussen (Genera *Orchidacearum*), the plant herein described is most likely a complex hybrid between *Miltonia, Oncidium*, and *Brassia* species, hence called x *Aliceara.*

All x *Aliceara* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth), with two leaves on each side. The peduncles vary in size from 20-70 cm.

x *Aliceara* orchids are used as flowering potted plants for home or interiorscape. x *Aliceara* produces upright or pendent lateral racemes or panicles, often with many showy flowers which open in succession beginning with the lowermost. The flowers possess three sepals and two petals, the lateral ones being alike and having a peculiar labellum. Flower colors include various shades of pink, purple, white, yellow, and red-brown.

x *Aliceara* orchids are typically propagated from tissue culture. Asexual propagation of x *Aliceara* is often done from off-shoots which arise from the lower bracts of the inflorescence. The resulting plants are detached from the mother plants and may be planted in a suitable substrate.

The new x *Aliceara* 'CAMBAMIM' is particularly characterized by its attractive and unique large, creamy-white flowers with dark red flecks and large, undulated white lips with 1-3 dark red flecks at the center, economical propagation by tissue culture, early flowering, and a plant dimension suitable for packaging and shipping to the market.

'CAMBAMIM' is a product of a planned breeding program conducted by the inventor in Bleiswijk, The Netherlands.

The new x *Aliceara* 'CAMBAMIM' originated from a cross made by the inventor in September 2009 in Bleiswijk, The Netherlands. The female parent is a white-brown x *Aliceara* pot plant named '60000-0593' (unpatented) and the male parent is a *Miltonia* plant named '60000-0529' (unpatented) with brown flowers and white lips. A single plant was selected by the inventor from within the progeny of the stated cross-pollination in a controlled greenhouse in Bleiswijk, The Netherlands, in July 2012.

Asexual reproduction of 'CAMBAMIM' by meristem tissue culture since 2012 in Bleiswijk, The Netherlands, has demonstrated that the new variety reproduces true to type with all of the characteristics, as herein described, firmly fixed and retained through successive generations.

Community Plant Variety Rights for this variety have been applied for in the European Union on Nov. 20, 2018, by Applicant who obtained the subject matter disclosed directly from the inventor. 'CAMBAMIM' has not been made publicly available or sold anywhere in the world prior to the effective filing date of this application with the exception of sales or disclosures made one year or less before the effective filing date of this claimed invention by Applicant who obtained 'CAMBAMIM' directly from the inventor.

SUMMARY OF THE INVENTION

The following are the most outstanding and distinguishing characteristics of this new cultivar when grown under normal horticultural practices in Bleiswijk, The Netherlands.

1) Large, cream-white flowers with dark red flecks and large, undulated white lips with 1-3 dark red flecks;
2) 1-3 peduncles;
3) Peduncle is long and sturdy;
4) The shape of the leaf is lanceolate and elongated to very elongated; and
5) Plants are propagated by meristem tissue culture.

DESCRIPTION OF THE PHOTOGRAPHS

This new x *Aliceara* plant is illustrated by the accompanying photographs which show the overall plant habit including blooms, buds, and foliage of the plant. The colors shown are as true as can be reasonably obtained by conventional photographic procedures. The photographs are of a 70-week old plant grown in a greenhouse in Bleiswijk, The Netherlands, in July 2019.

DESCRIPTION OF THE NEW VARIETY

Figure 1:
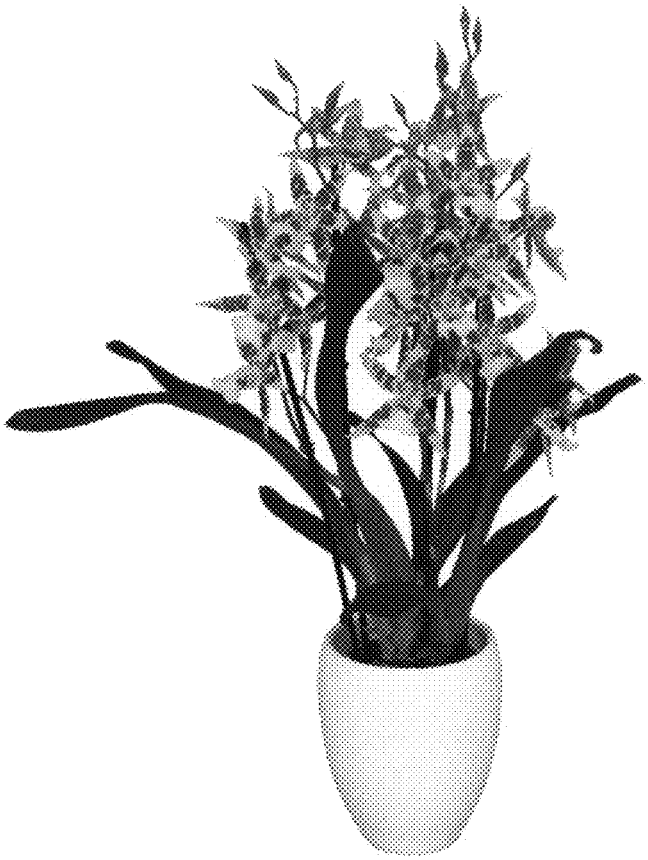
FIG. 1 shows the overall plant habit, including blooms, buds, and foliage of 'CAMBAMIM'.
Figure 2:
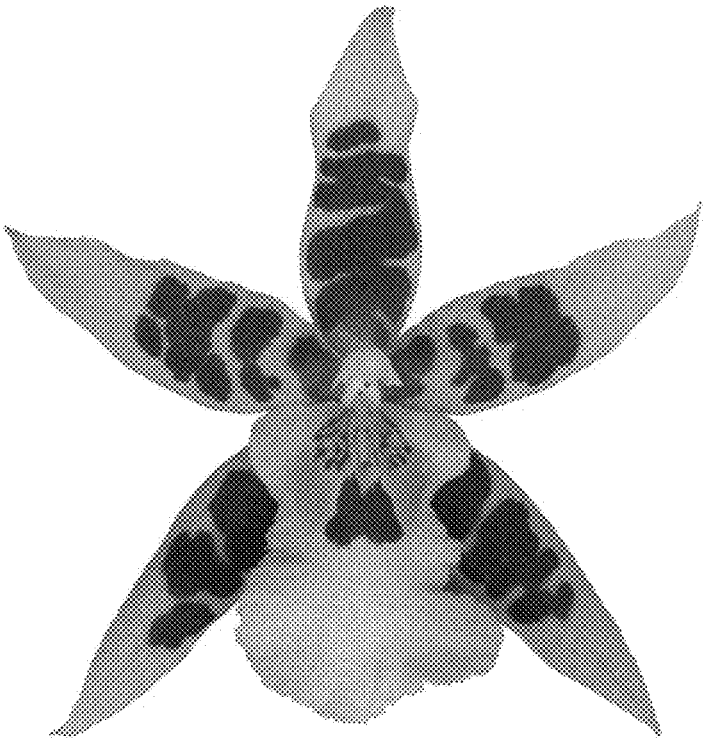
FIG. 2 shows a close-up of a flower of 'CAMBAMIM'.
Figure 3:
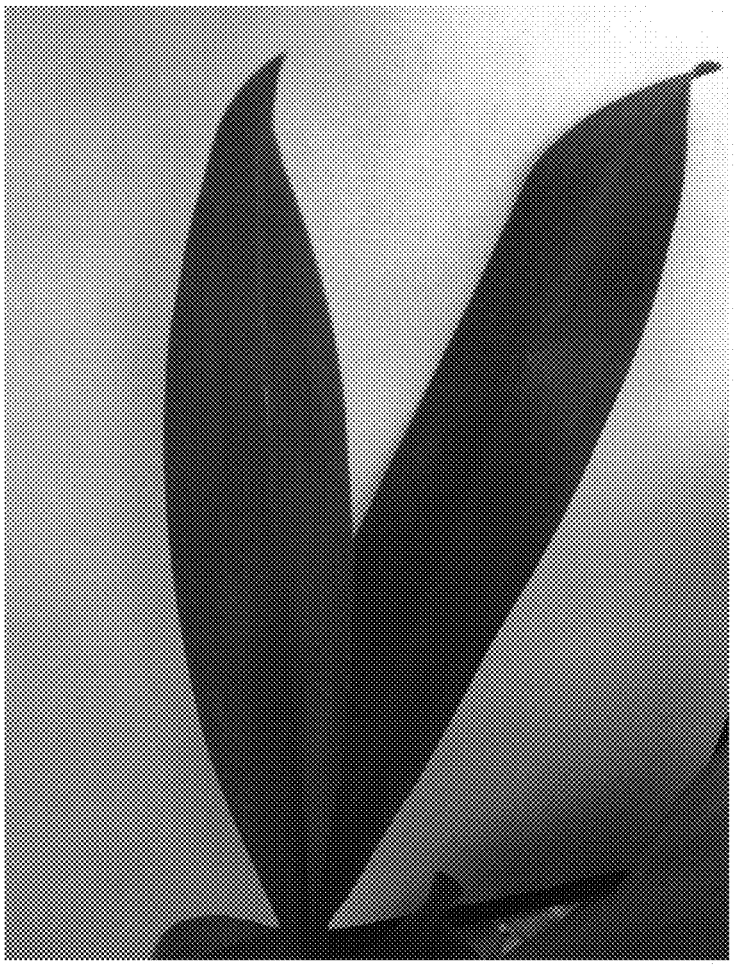
FIG. 3 shows a close-up of the leaves of 'CAMBAMIM'.

The following detailed description sets forth the distinctive characteristics of 'CAMBAMIM'. The data which define these characteristics were collected from asexual reproductions carried out in Bleiswijk, The Netherlands. The plant history was taken on 70-week old plants which were planted from tissue culture to a plug and then to 12-centimeter pots and grown in a greenhouse between 20° C. to 25° C. Observations were made in July 2019. Color readings were taken under 4000-6000 lux natural light in the greenhouse. Color references are primarily to The RHS Colour Chart of The Royal Horticultural Society of London (RHS) (2015).

DETAILED BOTANICAL DESCRIPTION

Classification:

*Family.*—Orchidaceae.

*Botanical.*—x *Aliceara.*

*Common name.*—Cambria.

*Variety name.*—'CAMBAMIM'.

Parentage:

*Female parent.*—x *Aliceara* cultivar '60000-0593' (unpatented).

*Male parent.*—*Miltonia* cultivar '60000-0529' (unpatented).

Propagation:

*Type.*—Meristem tissue culture.

Plant:

*Crop time* (*time to produce a finished flowering plant*).—50 to 70 weeks for a 12-cm pot.

*Growth habit of peduncle.*—Upright with raceme inflorescence, green leaves.

*Height* (*including pot, including inflorescence*).—60.0 cm to 70.0 cm.

*Width* (*measured from leaf tips*).—35.0 cm to 45.0 cm.

*Vigor.*—Strong.

Roots:

*Root description.*—Greyed-yellow (RHS 164D) colored roots lightly branching with light yellow (RHS 162D) growing tips.

Pseudobulb:

*Number of pseudobulbs.*—1 to 4.

*Shape.*—Laterally compressed ovoid.

*Length.*—8.0 cm to 12.0 cm.

*Width.*—3.0 cm to 4.0 cm.

*Thickness.*—1.5 cm to 2.5 cm.

*Color.*—Green (RHS 146C).

Leaves:

*Mature leaves.*—Quantity per pseudobulb: 5 to 7 leaves are produced before flowering. Length (fully expanded): 30.0 cm to 40.0 cm. Width: 3.5 cm to 4.5 cm. Shape: Lanceolate. Base shape: Elongated to very elongated. Apex: Acute. Leaf margin: Entire. Color: Upper surface: RHS 147A. Lower surface: RHS 146B. Texture: Upper surface: Smooth. Lower surface: Smooth. Thickness: 0.4 mm to 0.5 mm. Venation: Pattern: Parallel. Color of the midvein: Upper surface: RHS 147A. Lower surface: RHS 147B.

Peduncle:

*Quantity per plant.*—2 to 4.

*Number of flowers per peduncle.*—6 to 10.

*Length.*—From 50.0 cm to 60.0 cm.

*Diameter.*—3.0 mm to 4.5 mm.

*Strength.*—Strong.

*Aspect.*—Upright.

*Texture.*—Smooth.

*Color.*—Green (RHS 146A).

*Internode length.*—40.0 mm to 80.0 mm.

*Number of branches.*—0.

*Callosities.*—None.

Inflorescence description:

*Appearance.*—Raceme inflorescence with bilaterally symmetrical flowers that open in succession beginning with the lowermost flower.

*Inflorescence size.*—Height (from base to tip): 200.0 mm to 300.0 mm. Diameter: 130.0 mm to 150.0 mm.

*Flowering time.*—First flowers can be expected 4 to 8 months after planting in a 12-cm pot.

*Flower.*—Height: 80.0 mm to 100.0 mm. Diameter: 80.0 mm to 90.0 mm.

*Flower longevity.*—On the plant: 3 to 6 weeks.

*Fragrance.*—Present.

*Petals.*—Shape: Elliptic. Apex: Acute. Margin: Undulated (widely wavy). Texture (both upper and lower surfaces): Smooth. Length (from base to tip): 45.0 mm to 50.0 mm. Width: 12.0 mm to 15.0 mm. Color (when fully opened): Upper surface: Basic color: Cream white (RHS 157C). Over color: Dark red flecks (RHS 59A); few flecks, medium to large size. Lower surface: Basic color: Green-white (RHS 157B). Over color: Light green (RHS 157A) at the base.

*Dorsal sepal.*—Shape: Elliptic. Apex: Acute. Margin: Entire. Texture (both upper and lower surfaces): Smooth. Length (from base to tip): 47.0 mm to 49.0 mm. Width: 10.0 mm to 15.0 mm. Color (when fully opened): Upper surface: Basic color: Cream white (RHS 157C). Over color: Dark red flecks (RHS 59A); few flecks, medium to large size. Lower surface: Basic color: Green-white (RHS 157B). Over color: Light green (RHS 157A) at the base.

*Lateral sepals.*—Shape: Elliptic. Margin: Entire. Texture (both upper and lower surfaces): Smooth. Length (from base to tip): 50.0 mm to 55.0 mm. Width: 10.0 mm to 14.0 mm. Color (when fully opened): Upper surface: Basic color: Cream white (RHS 157C). Over color: Dark red flecks (RHS 59A); few flecks, medium to large size. Lower surface: Basic color: Green-white (RHS 157B). Over color: Light green (RHS 157A) at the base.

*Labellum* (*lip*).—Length: 40.0 mm to 45.0 mm. Width: 30.0 mm to 35.0 mm. Apex: Serrulate. Margin: Serrulate. Texture (both upper and lower surfaces): Smooth. Color: Upper surface: White (RHS 155C) and 1 to 3 (depending on the flower) dark red flecks (RHS 59A) toward the center with a pale yellow (RHS 9C) around the callus and a diluting purplish-red region (RHS N77B) toward the callus. Lower surface: White (RHS 155C).

*Callus.*—Color: Pale yellow (RHS 155C). Shape: Indescribable. Average size: Indescribable. Average number of protuberance: 5 to 10.

Reproductive organs:

*Arrangement.*—The stamens, style, and stigmas are fused into a single, short structure called the column, possessing one terminal anther with pollen grains united into pollinia, which are covered by an anther cap. The stigma is located under the column behind the pollinia. The ovary is inferior with three carpels present.

*Column.*—Length: 9.0 mm to 11.0 mm. Diameter: 4.0 mm to 6.0 mm. Color: Cream white (RHS 157C). Wings: Absent.

*Cap.*—Average size: 3.0 mm to 4.0 mm. Shape: Oval cup shape. Color: Cream white (RHS 157C).

*Pollinia.*—Quantity: 2. Diameter: 1.0 mm to 1.2 mm. Color: Yellow-orange (RHS 14B).

*Ovary.*—Length: 15.0 mm to 25.0 mm. Diameter: 3.0 mm to 4.0 mm.

*Pedicel.*—Length: 30.0 mm to 35.0 mm. Diameter: 3.0 mm to 4.0 mm. Color: Green (RHS 144B).

Disease, pest, and stress resistance: No specific resistance or susceptibility observed to date.

Temperature tolerance: Not observed to date.

COMPARISON WITH PARENTAL LINES AND SIMILAR VARIETY

'CAMBAMIM' differs from female parent '60000-0593' (unpatented) in that 'CAMBAMIM' has cream-white flowers with a spotted pattern, whereas '60000-0593' has white flowers with a brown center that are evenly colored around the flower center.

'CAMBAMIM' differs from male parent '60000-0529' (unpatented) in that 'CAMBAMIM' has cream-white flowers with a spotted pattern, whereas '60000-0529' has yellow-brown flowers with large spots.

'CAMBAMIM' is most similar to the commercial x *Aliceara* plant named 'CAMBIMWIK' (U.S. Plant Pat. No. 30,610). 'CAMBAMIM' differs from commercial variety 'CAMBIMWIK' in that 'CAMBAMIM' has cream-white petals with a dark red over color, whereas 'CAMBIMWIK' has dark red petals with a purple-red over color toward the tip and a green tip. Additionally, 'CAMBAMIM' has a small blotch on the upper part of the lip, just below the callus and very small spots around the callus, whereas 'CAMBIMWIK' has a large central blotch around the upper part of the lip with a white creamy edge.

I claim:

1. A new and distinct variety of x *Aliceara* plant named 'CAMBAMIM', substantially as described and illustrated herein.

* * * * *